United States Patent
Casset et al.

(10) Patent No.: US 10,638,930 B2
(45) Date of Patent: May 5, 2020

(54) SYSTEMS AND METHODS FOR LEVERAGING IEGM COUPLES TO DETERMINE ABLATION SITES

(71) Applicant: PACESETTER, INC., Sylmar, CA (US)

(72) Inventors: Cyrille Casset, Saint Selve (FR); Jan Mangual-Soto, Rho (IT); Louis-Philippe Richer, Montreal (FR); Chunlan Jiang, Crystal, MN (US); Craig Markovitz, Leipzig (DE)

(73) Assignee: PACESETTER, INC., Sylmar, CA (US)

( * ) Notice: Subject to any disclaimer, the term of this patent is extended or adjusted under 35 U.S.C. 154(b) by 135 days.

(21) Appl. No.: 15/851,352

(22) Filed: Dec. 21, 2017

(65) Prior Publication Data

US 2019/0192002 A1    Jun. 27, 2019

(51) Int. Cl.
| | |
|---|---|
| *A61B 5/00* | (2006.01) |
| *A61N 1/05* | (2006.01) |
| *A61B 18/14* | (2006.01) |
| *A61B 5/042* | (2006.01) |
| *A61N 1/362* | (2006.01) |
| *A61B 5/15* | (2006.01) |
| *A61B 18/00* | (2006.01) |
| *A61B 17/00* | (2006.01) |

(52) U.S. Cl.
CPC .......... *A61B 5/0031* (2013.01); *A61B 5/0422* (2013.01); *A61B 18/1492* (2013.01); *A61N 1/057* (2013.01); *A61B 5/15087* (2013.01); *A61B 5/6869* (2013.01); *A61B 5/6882* (2013.01); *A61B 2017/00053* (2013.01); *A61B 2018/00839* (2013.01); *A61N 1/3627* (2013.01)

(58) Field of Classification Search
CPC . A61B 5/0031; A61B 5/6869; A61B 5/15087; A61B 5/6882
See application file for complete search history.

(56) References Cited

U.S. PATENT DOCUMENTS

2012/0165811 A1* 6/2012 Gillberg ............... A61N 1/3621
606/41

* cited by examiner

*Primary Examiner* — Catherine M Voorhees
*Assistant Examiner* — Roland Dinga
(74) *Attorney, Agent, or Firm* — Dean D. Small; The Small Patent Law Group, LLC

(57) ABSTRACT

The present disclosure provides systems and methods for determining a proposed ablation site in a cardiac chamber. A system includes an implanted device configured to record a plurality of intracardiac electrogram (IEGM) couples, and a mapping and ablation system communicatively coupled to the implanted device. The mapping and ablation system is configured to receive the recorded plurality of IEGM couples from the implanted device, calculate a parameter for each of the plurality of IEGM couples, determine, based on the calculated parameters, an area of origin for each IEGM couple, and determine an intersection between the determined areas of origin, wherein the intersection represents the proposed ablation site in the cardiac chamber.

24 Claims, 15 Drawing Sheets

SYSTEMS AND METHODS FOR LEVERAGING IEGM COUPLES TO DETERMINE ABLATION SITES

A. FIELD OF THE DISCLOSURE

The present disclosure relates generally to cardiac stimulation systems, and more particularly to transmitting data between an implanted device and a mapping and ablation system to propose one or more ablation sites.

B. BACKGROUND ART

Heart failure (HF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats, and the valves regulating blood flow may develop leaks, allowing regurgitation or backflow of blood. The impairment of arterial circulation deprives vital organs of oxygen and nutrients. Fatigue, weakness, and inability to carry out daily tasks may result. Not all HF patients suffer debilitating symptoms immediately. Some may live actively for years. Yet, with few exceptions, the disease is relentlessly progressive. As HF progresses, it tends to become increasingly difficult to manage.

Heart failure may result in patients experiencing ventricular arrhythmias, such as ventricular tachycardia (VT). Ventricular arrhythmias may be treated by ablation, in which a physician identifies and ablates particular ventricular zones. However, in the absence of clear clinical information on the arrhythmia to be treated, physicians may end up ablating areas that are not responsible for the arrhythmia and/or missing the arrhythmogenic zone. For example, it may be difficult to obtain an electrocardiogram while a patient is in a state of VT when that patient presents with significant myocardial excitability (e.g., incessant triggering of multiple VTs) or relatively weak/non-tolerated VT (resulting in inability to trigger VT to identify the arrhythmogenic zone).

Notably, rhythm data obtained during an exploration portion of an ablation procedure is generally not recorded by implantable defibrillators. This limits the use of exam results to guide reprogramming of detection zones of the implantable defibrillators (e.g., VT zones, ventricular fibrillation (VF) zones) or applied treatments (e.g., antitachycardia pacing (ATP) and shock treatment).

Thus, in at least some known systems, there is no direct link between data collected by an implanted device (e.g., an implantable defibrillator) and data collected during an electrophysiology (EP) examination. This may negatively impact patient management during both the EP examination and long-term follow-up using the implanted device.

BRIEF SUMMARY OF THE DISCLOSURE

In one embodiment, the present disclosure is directed to a system for determining a proposed ablation site in a cardiac chamber. The system includes an implanted device configured to record a plurality of intracardiac electrogram (IEGM) couples, and a mapping and ablation system communicatively coupled to the implanted device. The mapping and ablation system is configured to receive the recorded plurality of IEGM couples from the implanted device, calculate a parameter for each of the plurality of IEGM couples, determine, based on the calculated parameters, an area of origin for each IEGM couple, and determine an intersection between the determined areas of origin, wherein the intersection represents the proposed ablation site in the cardiac chamber.

In another embodiment, the present disclosure is directed to a mapping and ablation system for determining a proposed ablation site in a cardiac chamber. The mapping and ablation system includes a memory device, and a processor communicatively coupled to the memory device, the processor configured to receive a plurality of intracardiac electrogram (IEGM) couples recorded by an implanted device, calculate a parameter for each of the plurality of IEGM couples, determine, based on the calculated parameters, an area of origin for each IEGM couple, and determine an intersection between the determined areas of origin, wherein the intersection represents the proposed ablation site in the cardiac chamber.

In another embodiment, the present disclosure is directed to a method for determining a proposed ablation site in a cardiac chamber. The method includes receiving, at a mapping and ablation system, a plurality of intracardiac electrogram (IEGM) couples recorded by an implanted device, calculating, using the mapping and ablation system, a parameter for each of the plurality of IEGM couples, determining, using the mapping and ablation system, based on the calculated parameters, an area of origin for each IEGM couple, and determining, using the mapping and ablation system, an intersection between the determined areas of origin, wherein the intersection represents the proposed ablation site in the cardiac chamber.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for determining a proposed ablation site in a cardiac chamber. An implanted device records a plurality of Intracardiac electrogram (IEGM) couples. A mapping and ablation system communicatively coupled to the implanted device receives the recorded plurality of IEGM couples from the implanted device, and calculates a parameter for each of the plurality of IEGM couples. Based on the calculated parameters, the mapping and ablation system determines an area of origin for each IEGM couple, and determines an intersection between the determined areas of origin, the intersection representing the proposed ablation site in the cardiac chamber.

Figure 1A:
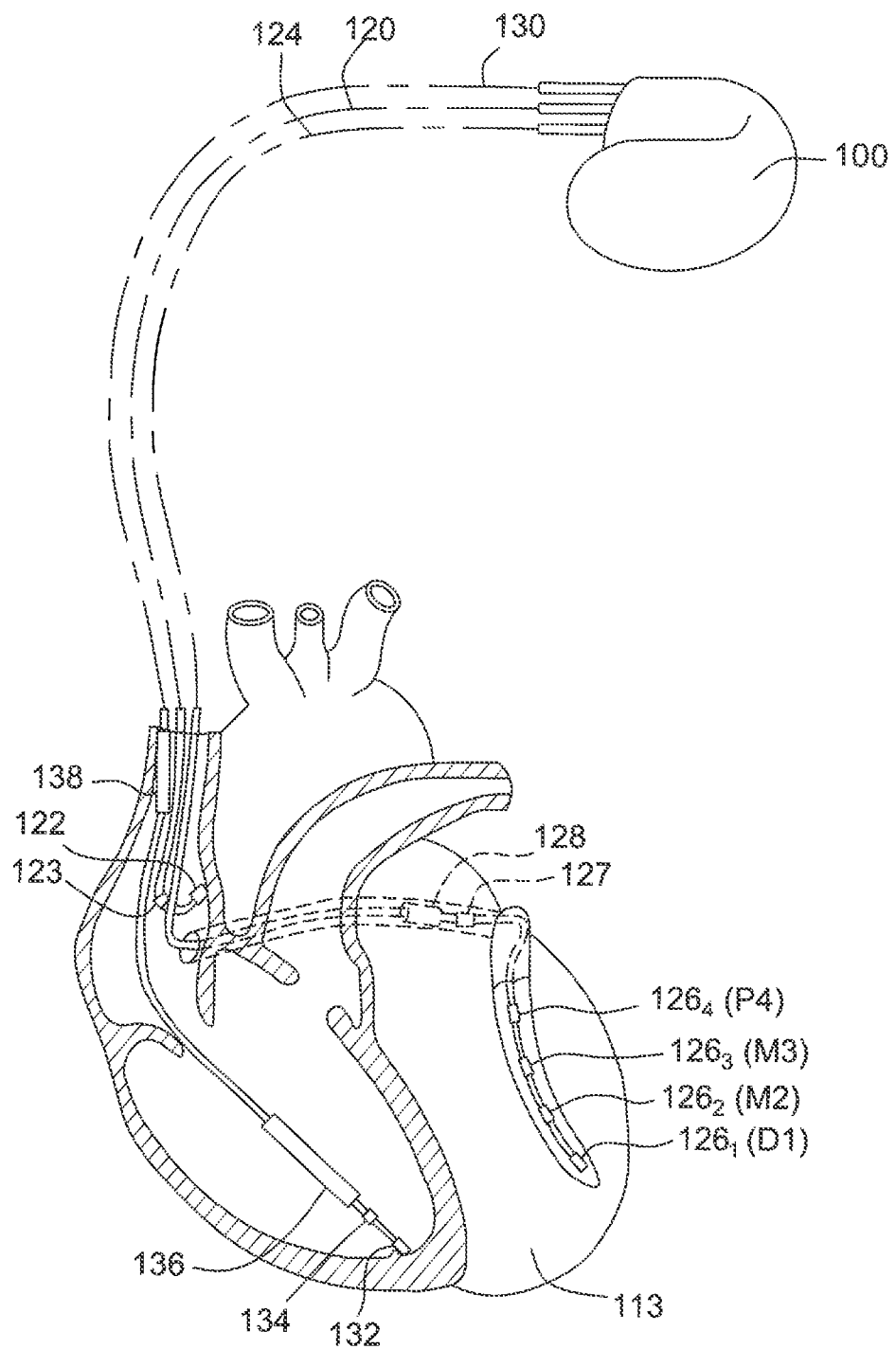
FIG. 1A is a simplified, partly cutaway view illustrating an implantable stimulation device in electrical communication with at least three leads implanted into a patient's heart for delivering multi-chamber stimulation and shock therapy and sensing cardiac activity.
Figure 1B:
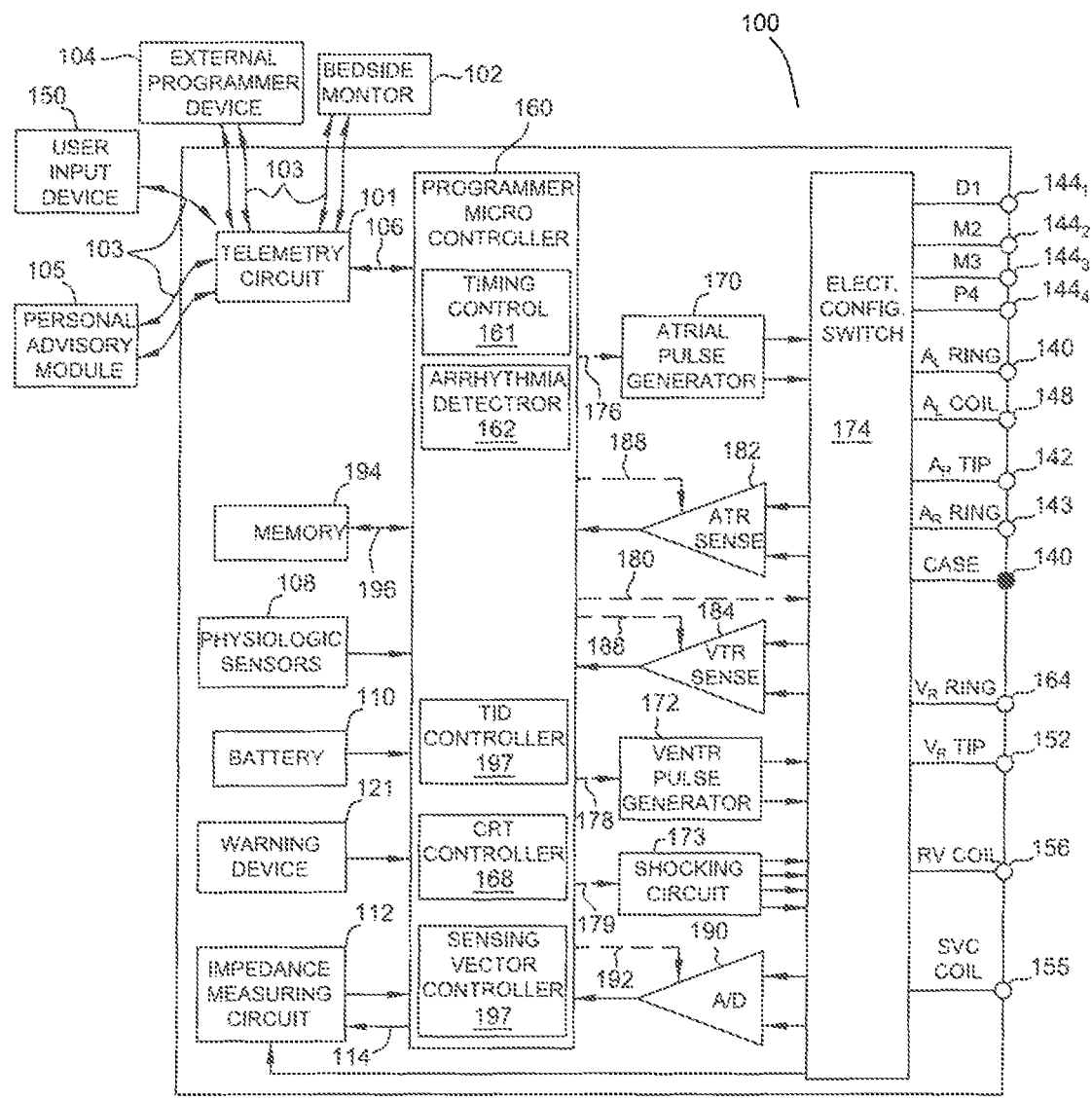
FIG. 1B is a functional block diagram of the multi-chamber implantable stimulation device of FIG. 1A, illustrating the basic elements that provide pacing stimulation, cardioversion, and defibrillation in four chambers of the heart.

With reference to FIGS. 1A and 1B, a description of an example pacemaker/implantable cardioverter-defibrillator (ICD) 100 will now be provided. FIG. 1A is a simplified block diagram of pacemaker/ICD 100, which is a dual-chamber stimulation device capable of treating both fast and slow arrhythmias with stimulation therapy, including cardioversion, defibrillation, and pacing stimulation, including multipoint pacing (MPP). To provide atrial chamber pacing stimulation and sensing, pacemaker/ICD 100 is shown in electrical communication with a heart 113 by way of a right atrial (RA) lead 120 having an atrial tip electrode 122 and an atrial ring electrode 123 implanted in the atrial appendage. Pacemaker/ICD 100 is also in electrical communication with heart 113 by way of a right ventricular (RV) lead 130 having, in this embodiment, a ventricular tip electrode 132, a RV ring electrode 134, a RV coil electrode 136, and a superior vena cava (SVC) coil electrode 138. Typically, RV lead 130 is transvenously inserted into the heart so as to place RV coil electrode 136 in the RV apex, and SVC coil electrode 138 in the superior vena cava. Accordingly, RV lead 130 is capable of receiving cardiac signals, and delivering stimulation in the form of pacing and shock therapy to the right ventricle (also referred to as the RV chamber).

To sense left atrial and ventricular cardiac signals and to provide left chamber pacing therapy, pacemaker/ICD 100 is coupled to a multi-pole left ventricular (LV) lead 124 designed for placement in the "CS region" for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the coronary sinus (CS), great cardiac vein, left marginal vein, left posterior ventricular vein, middle cardiac vein, small cardiac vein, and/or any other cardiac vein accessible by the CS. Accordingly, an example LV lead 124 is designed to receive atrial and ventricular cardiac signals and to deliver left ventricular pacing therapy using a set of four LV electrodes $126_1$, $126_2$, $126_3$, and $126_4$ (thereby providing a quadra-pole lead), left atrial pacing therapy using at least a LA ring electrode 127, and shocking therapy using at least a LA coil electrode 128. In some embodiments, LV lead 124 includes LV electrodes $126_1$, $126_2$, $126_3$, and $126_4$, but does not include LA ring and coil electrodes 127 and 128. Such a lead can be, e.g., the Quartet™ left ventricular pacing lead developed by Abbott Laboratories, which includes four pacing electrodes on the left ventricular lead—enabling up to ten pacing configurations LV electrode $126_1$ is shown as being the most "distal" LV electrode (with relation to how far the electrode is from where LV lead 124 connects to pacemaker/ICD 100). For example LV electrode $126_1$ may be located at the apex of the left ventricle. LV electrode $126_4$ is shown as being the most "proximal" LV electrode. For example LV electrode $126_4$ may be located at the base of the left ventricle. LV electrodes $126_2$ and $126_3$ are shown as being "middle" LV electrodes, between distal and proximal LV electrodes $126_1$ and $126_4$. Accordingly, the four LV electrodes $126_1$, $126_2$, $126_3$, and $126_4$ can be referred to respectively as electrodes D1, M2, M3 and P4 (where "D" stands for "distal", "M" stands for "middle", and "P" stands from "proximal", and the numbers are arranged from most distal to most proximal). It is also possible that more or fewer LV electrodes are provided. However, for much of the remaining discussion, it will be assumed that the multi-pole LV lead 124 includes four LV electrodes $126_1$, $126_2$, $126_3$, and $126_4$ (i.e., LV electrodes D1, M2, M3 and P4, respectively).

LV electrodes $126_1$, $126_2$, $126_3$, and $126_4$ can be used to provide various pacing vectors and sensing vectors. Some of the vectors are intraventricular LV vectors (vectors between two LV electrodes); whereas others are interventricular vectors (e.g., vectors between an LV electrode and RV coil electrode 136). Below is a list of exemplary vectors that can be used for pacing and/or sensing using LV electrodes D1, M2, M3 and P4 with and without the RV coil electrode 136. In the following list, the first electrode in each row (i.e., the electrode to the left of the arrow) is assumed to be connected as the cathode, and the second electrode in each row (i.e., the electrode to the right of the arrow) is assumed to be connected as the anode, but that need not be the case, especially where neither electrode is a coil.

D1→RV coil
M2→RV coil
M3→RV coil
P4→RV coil
D1→M2
D1→P4
M2→P4
M3→M2
M3→P4
P4→M2

Alternative and/or additional vectors, other than those listed above, can be used for pacing and/or sensing. Although only three leads are shown in FIG. 1A, it should also be understood that additional leads (with one or more pacing, sensing, and/or shocking electrodes) might be used and/or additional electrodes might be provided on the leads already shown, such as additional electrodes on the RV or LV lead. It is also possible that less than three leads be used.

A simplified block diagram of internal components of pacemaker/ICD 100 is shown in FIG. 1B. While a particular pacemaker/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. A housing 140 for pacemaker/ICD 100, shown schematically in FIG. 1B, is often referred to as the "can", "case" or "case electrode" and may be programmably selected to act as the return electrode for all "unipolar" modes. Housing 140 may further be used as a return electrode alone or in combination with one or more of coil electrodes, 128, 136 and 138 for shocking purposes. Housing 140 further includes a connector (not shown) having a plurality of terminals. 142, 143, 144$_1$-144$_4$, 146, 148, 152, 154, 156 and 158 (shown schematically and, for convenience, the names of the electrodes to which they are connected are shown next to the terminals). As such, to achieve RA sensing and pacing, the connector includes at least an RA tip terminal (A$_R$ TIP) 142 adapted for connection to the atrial tip electrode 122 and an RA ring (A$_R$ RING) electrode 143 adapted for connection to atrial ring electrode 123. To achieve left chamber sensing, pacing and shocking, the connector includes an LV tip terminal 144$_1$ adapted for connection to the D1 electrode and additional LV electrode terminals 144$_2$, 144$_3$ and 144$_4$ terminals adapted for connection to the M2, M3 and P4 electrodes of quadra-pole LV lead 124.

The connector also includes an LA ring terminal (A$_L$ RING) 146 and an LA shocking terminal (A$_L$ COIL) 148, which are adapted for connection to LA ring electrode 127 and the LA coil (A$_L$ COIL) electrode 128, respectively. To support right chamber sensing, pacing and shocking, the connector further includes an RV tip terminal (V$_R$ TIP) 152, an RV ring terminal (V$_R$ RING) 154, an RV shocking terminal (V$_R$ COIL) 156, and an SVC shocking terminal (SVC COIL) 158, which are adapted for connection to ventricular tip electrode 132, RV ring electrode 134, RV coil electrode 136, and SVC coil electrode 138, respectively.

At the core of pacemaker/ICD 100 is a programmable microcontroller 160, which controls the various modes of stimulation therapy. As is well known in the art, microcontroller 160 (also referred to herein as a control unit or controller) typically includes a microprocessor, or equivalent control circuitry, designed specifically for controlling the delivery of stimulation therapy and may further include RAM or ROM memory, logic and timing circuitry, state machine circuitry, and I/O circuitry. Typically, microcontroller 160 includes the ability to process or monitor input signals (data) as controlled by a program code stored in a designated block of memory.

As shown in FIG. 1B, an atrial pulse generator 170 (controlled by a control signal 176) and a ventricular pulse generator 172 (controlled by a control signal 178) generate pacing stimulation pulses for delivery by RA lead 120, RV lead 130, and/or LV lead 124 via an electrode configuration switch 174. Microcontroller 160 includes timing control circuitry 161 to control the timing of the stimulation pulses, including, but not limited to, pacing rate, atrio-ventricular (AV) delay, interatrial conduction (AA) delay, interventricular conduction (W) delay and/or intraventricular delay (e.g., LV1-LV2 delay). Timing control circuitry 161 can also keep track of timing of refractory periods, blanking intervals, noise detection windows, evoked response detection windows, alert intervals, marker channel timing, etc. Microcontroller 160 further includes an arrhythmia detector 162 that can be utilized by pacemaker/ICD 100 for determining desirable times to administer various therapies.

Microcontroller 160 is also shown as including a sensing vector controller 169 that can be used, e.g., to control the electrode configuration switch 174 (e.g., via control signals 180) to selectively connect specific electrode(s) to sensing circuits 182 or 184 as a cathode or an anode, to achieve the various sensing vectors that are used to obtain intracardiac electrograms (IEGMs) in accordance with embodiments described herein. Where multiple sensing vectors are being used to obtain a plurality of IEGMs indicative of cardiac electrical activity at a plurality of ventricular regions, sensing circuit 184 may include multiple channels (e.g., duplicate circuitry) to enable sensing of more than one ventricular IEGM signal at the same time, and/or sensing circuit 184 may use time divisional multiplexing to sense more than one ventricular IEGM signal.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

Switch 174 includes a plurality of switches for connecting the desired electrodes to the appropriate I/O circuits, thereby providing complete electrode programmability. Accordingly, switch 174, in response to a control signal 180 from microcontroller 160, determines the polarity of the stimulation pulses (e.g., unipolar, bipolar, combipolar (e.g., using unipolar leads in the atrium and ventricle and performing atrial sensing in a bipolar way using the ventricular lead tip as an indifferent electrode), etc.) by selectively closing the appropriate combination of switches (not shown) as is known in the art. The switch also switches among the various LV electrodes.

Atrial sensing circuits 182 (controlled by a control signal 186) and ventricular sensing circuits 184 (controlled by a control signal 188) may also be selectively coupled to RA lead 120, LV lead 124, and RV lead 130, through switch 174 for detecting the presence of cardiac activity in each of the four chambers of the heart. Accordingly, the atrial (ATR. SENSE) and ventricular (VTR. SENSE) sensing circuits, 182 and 184, may include dedicated sense amplifiers, multiplexed amplifiers or shared amplifiers. Switch 174 determines the "sensing polarity" of the cardiac signal by selectively closing the appropriate switches, as is also known in the art. In this way, a clinician may program the sensing polarity independent of the stimulation polarity. Each sensing circuit, 182 and 184, preferably employs one or more low power, precision amplifiers with programmable gain and/or automatic gain control, bandpass filtering, and a threshold detection circuit, as known in the art, to selectively sense the cardiac signal of interest. The automatic gain control enables pacemaker/ICD 100 to deal effectively with the difficult problem of sensing the low amplitude signal characteristics of atrial or ventricular fibrillation. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are applied to the inputs of an analog-to-digital (A/D) data acquisition system 190 (controlled by a control signal 192). Data acquisition system 190 is configured to acquire intracardiac electrogram signals, convert the raw analog data into a digital signal, and store the digital signals for later processing and/or telemetric transmission to an external programmer device 104 or a bedside monitor 102 or personal advisory module. Data acquisition system 190 is coupled to RA lead 120, LV lead 124, and RV lead 130 through switch 174 to sample cardiac signals across any pair of desired electrodes. Microcontroller 160 is further coupled to a memory 194 by a suitable data/address bus 196, wherein the programmable operating parameters used by microcontroller 160 are stored and modified, as required, in order to customize the operation of pacemaker/ICD 100 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each pacing and shocking pulse to be delivered to the patient's heart within each respective tier of therapy. Other pacing parameters include base rate, rest rate and circadian base rate.

Advantageously, the operating parameters of implantable pacemaker/ICD 100 may be non-invasively programmed into memory 194 through a telemetry circuit 101 in telemetric communication with external programmer device 104 or bedside monitor 102, such as a programmer, transtelephonic transceiver, or a diagnostic system analyzer. The telemetry circuit 101 is activated by the microcontroller by a control signal 106. Telemetry circuit 101 advantageously allows intracardiac electrograms and status information relating to the operation of pacemaker/ICD 100 (as contained in microcontroller 160 or memory 194) to be sent to external programmer device 104 and/or bedside monitor 102 through an established communication link 103. An internal warning device 121 (also referred to as a patient alert) may be provided for generating perceptible warning signals to the patient via vibration, voltage or other methods.

Pacemaker/ICD 100 further includes an accelerometer or other physiologic sensor 108, commonly referred to as a "rate-responsive" sensor because it is typically used to adjust pacing stimulation rate according to the exercise state of the patient. Pacemaker/ICD 100 additionally includes a battery 110 that provides operating power to the circuits shown in FIG. 1B. As further shown in FIG. 1B, pacemaker/ICD 100 is shown as having an impedance measuring circuit 112, which is enabled by the microcontroller 160 via a control signal 114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. Impedance measuring circuit 112 is advantageously coupled to switch 174 so that any desired electrode may be used.

In the case where pacemaker/ICD 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, microcontroller 160 further controls a shocking circuit 173 by way of a control signal 179. Shocking circuit 173 generates shocking pulses of low (up to 0.1 joules), moderate (0.1-10 joules) or high energy (11 to 40 joules or more), as controlled by the microcontroller 160. Such shocking pulses are applied to the heart of the patient through at least two shocking electrodes, and as shown in this embodiment, selected from LA coil electrode 128, RV coil electrode 136, and/or SVC coil electrode 138. Housing 140 may act as an active electrode in combination with RV coil electrode 136, or as part of a split electrical vector using SVC coil electrode 138 or LA coil electrode 128 (i.e., using RV coil electrode 136 as a common electrode).

In the exemplary embodiment, pacemaker/ICD 100 is capable of measuring one or more intracardiac electrogram (IEGM) vectors, as described herein. These IEGM vectors are used to propose ablation sites, as described herein.

Figure 2:
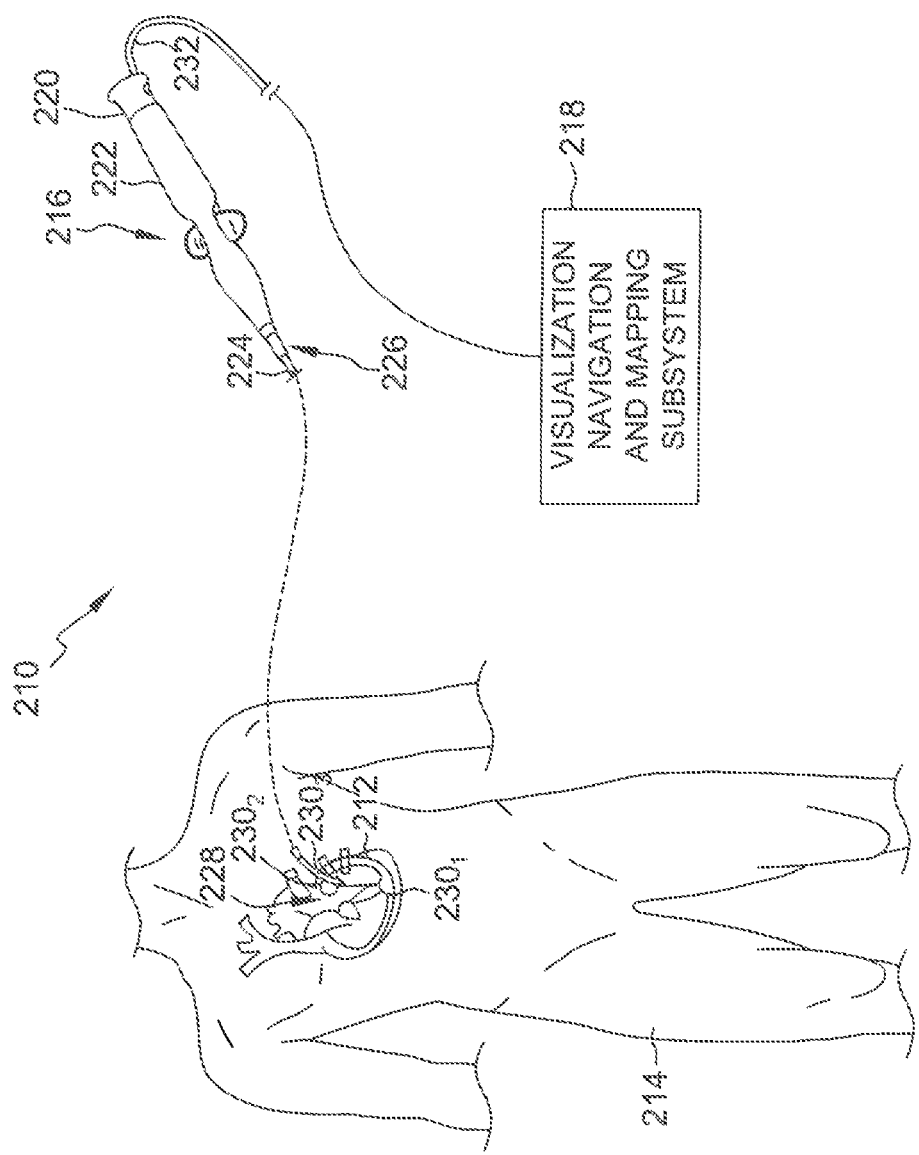
FIG. 2 is a schematic and diagrammatic view of a system for performing at least one of a diagnostic and a therapeutic medical procedure in accordance with present teachings.

FIG. 2 illustrates one exemplary embodiment of a mapping and ablation system 210 for performing one or more diagnostic and/or therapeutic functions on or for a tissue 212 of a body 214. In an exemplary embodiment, tissue 212 includes heart or cardiac tissue within a human body 214. It should be understood, however, that system 210 may find application in connection with a variety of other tissues within human and non-human bodies, and therefore, the present disclosure is not meant to be limited to the use of system 210 in connection with only cardiac tissue and/or human bodies.

System 210 may include a medical device (e.g., a catheter 216) and a subsystem 218 for the visualization, navigation, and/or mapping of internal body structures (hereinafter referred to as the "visualization, navigation, and mapping subsystem 218" or "subsystem 218").

In this embodiment, medical device includes a catheter 216, such as, for example, an electrophysiology catheter. In other exemplary embodiments, medical device may take a form other than catheter 216, such as, for example and without limitation, a sheath or catheter-introducer, or a catheter other than an electrophysiology catheter. For clarity and illustrative purposes only, the description below will be limited to embodiments of system 210 wherein medical device is a catheter (catheter 216).

Catheter 216 is provided for examination, diagnosis, and/or treatment of internal body tissues such as tissue 212. Catheter 216 may include a cable connector 220 or interface, a handle 222, a shaft 224 having a proximal end 226 and a distal end 228 (as used herein, "proximal" refers to a direction toward the end of catheter 216 near handle 222, and "distal" refers to a direction away from handle 222), and one or more sensors, such as, for example and without limitation, a plurality of electrodes 230 (i.e., $230_1$, $230_2$, ..., $230_N$), mounted in or on shaft 224 of catheter 216 at or near distal end 228 of shaft 224. The sensors may include, for example, impedance electrodes.

In this embodiment, each electrode 230 is configured to both acquire electrophysiological (EP) data corresponding to tissue 212, and to produce signals indicative of its three-dimensional (3-D) position (hereinafter referred to as "positioning data"). In another embodiment, catheter 216 may include a combination of electrodes 230 and one or more positioning sensors (e.g., electrodes other than electrodes 230 or magnetic sensors (e.g., coils)). In one such embodiment, electrodes 230 are configured to acquire EP data relating to tissue 212, while the positioning sensor(s) is configured to generate positioning data indicative of the 3-D position thereof, which may be used to determine the 3-D position of each electrode 230. In other embodiments, catheter 216 may further include other conventional components such as, for example and without limitation, steering wires and actuators, irrigation lumens and ports, pressure sensors, contact sensors, temperature sensors, additional electrodes and corresponding conductors or leads, and/or ablation elements (e.g., ablation electrodes, high intensity focused ultrasound ablation elements, and the like).

Connector 220 provides mechanical and electrical connection(s) for one or more cables 232 extending, for example, from visualization, navigation, and mapping subsystem 218 to one or more electrodes 230 or the positioning sensor(s) mounted on catheter 216. In other embodiments, connector 220 may also provide mechanical, electrical, and/or fluid connections for cables extending from other components in system 210, such as, for example, an ablation system and a fluid source (when catheter 216 includes an irrigated catheter). Connector 220 is disposed at proximal end 226 of catheter 216.

Handle 222 provides a location for a user to hold catheter 216 and may further provide means for steering or guiding shaft 224 within body 214. For example, handle 222 may include means to manipulate one or more steering wires extending through catheter 216 to distal end 228 of shaft 224 to steer shaft 224. It will be appreciated by those of skill in the art that the construction of handle 222 may vary. In other embodiments, the control of catheter 216 may be automated such as by being robotically driven or controlled, or driven and controlled by a magnetic-based guidance system. Accordingly, catheters controlled either manually or automatically are both within the spirit and scope of the present disclosure.

Shaft 224 is an elongate, tubular, and flexible member configured for movement within body 214. Shaft 224 supports, for example and without limitation, electrodes 230, other electrodes or positioning sensors mounted thereon, associated conductors, and possibly additional electronics used for signal processing or conditioning. Shaft 224 may also permit transport, delivery and/or removal of fluids (including irrigation fluids, cryogenic ablation fluids, and body fluids), medicines, and/or surgical tools or instruments. Shaft 224, which may be made from conventional materials such as polyurethane, defines one or more lumens configured to house and/or transport electrical conductors, fluids, or surgical tools. Shaft 224 may be introduced into a blood vessel or other structure within body 214 through a conventional introducer. Shaft 224 may then be steered or guided through body 214 to a desired location such as tissue 212.

Distal end 228 of shaft 224 may be the main portion of catheter 216 that contains electrodes 230 or other sensors for acquiring EP data and positioning data. As described above, in one embodiment, electrodes 230 may be configured to acquire both EP data and positioning data. In another embodiment, electrodes 230 may be configured to acquire EP data while one or more positioning sensors may be configured to acquire positioning data, which may then be used to determine the respective positions of electrodes 230. Regardless of whether the positioning data is acquired by electrodes 230 or by positioning sensors, distal end 228 may be arranged in a number of configurations that facilitate the efficient acquisition, measurement, collection, or the like of EP data from tissue 212.

Figure 3A:
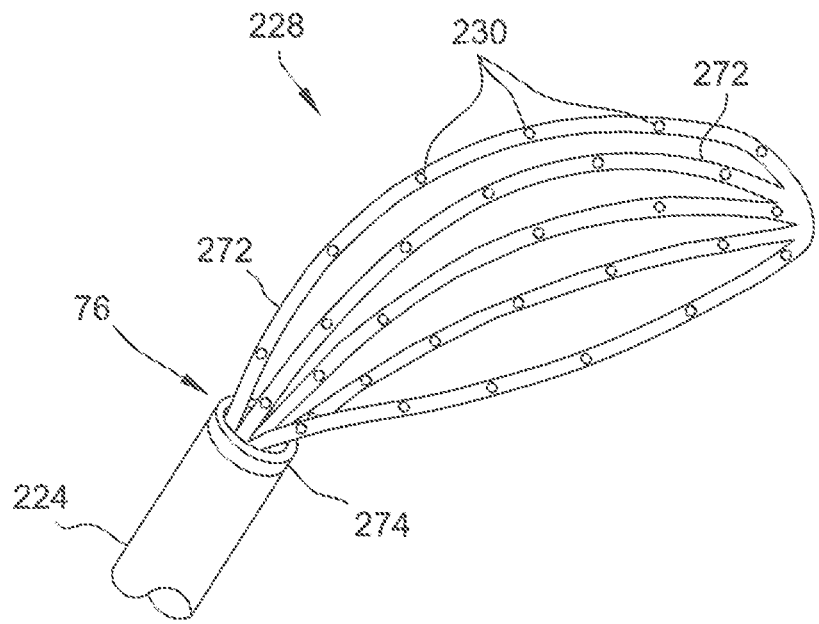
FIGS. 3A and 3B are isometric and side views, respectively, of a distal end of one embodiment of a medical device arranged in a matrix-like configuration.
Figure 3B:
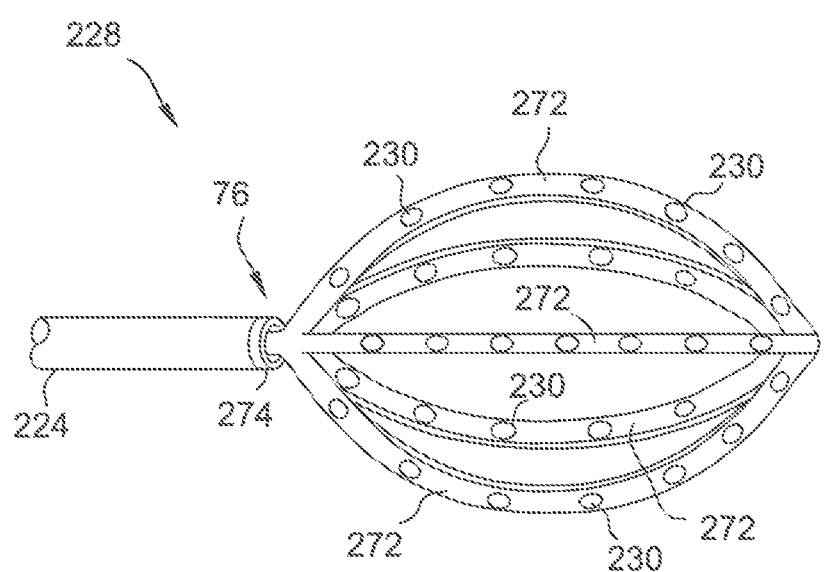

In one embodiment of the distal end 228 shown in FIGS. 3A and 3B, a matrix-like configuration may be provided with a high density of electrodes 230. FIG. 3A shows an isometric view of the matrix-like configuration, while FIG. 3B shows a side view. The matrix-like configuration may have a number of splines 272 arranged side by side, with each spline 272 having at least one electrode 230 mounted thereon. Longer splines may contain more electrodes 230 to maintain a consistent electrode density throughout the matrix-like configuration.

In the embodiment shown in FIGS. 3A and 3B, the matrix-like configuration may be cupped, almost as if to have a slight scoop as seen in FIG. 3A. In another embodiment (not shown), the matrix-like configuration may be substantially flat or planar, without any scoop-like feature. The matrix-like configuration shown in FIG. 3A in particular may be used to acquire at least some non-contact measurements. Another possible use of the matrix-like configuration would be to help diagnose arrhythmias and direct epicardial ablation therapies in the pericardial space.

In one embodiment, the matrix-like configuration along with other configurations of distal end 228 may collapse to a streamlined profile for insertion, manipulation, and removal from body 214. In addition, or in the alternative, distal end 228 may be at least partially concealed and transported within shaft 224 when not collecting data or performing a procedure. Shaft 224 may be more streamlined than distal end 228, and therefore may provide a better vehicle for transporting distal end 228 to and from tissue 212. Once at the intended site, distal end 228 may be deployed from shaft 224 to perform the intended procedures. Likewise, after the procedures are performed, distal end 228 may be re-concealed, at least in part, within shaft 224 for removal from body 214.

One exemplary way in which the matrix-like configuration is collapsible into a streamlined profile or fully or partially deployable is to allow outer splines 272 to translate modestly within shaft 224 while anchoring innermost splines 272 to shaft 224 at a point 274 at distal end 228 thereof. Moreover, for enhanced functionality, a joint 276 may be incorporated near point 274, either for providing flexibility or for selectively deflecting distal end 228, thereby allowing distal end 228 better access to tissue 212.

Figure 4:
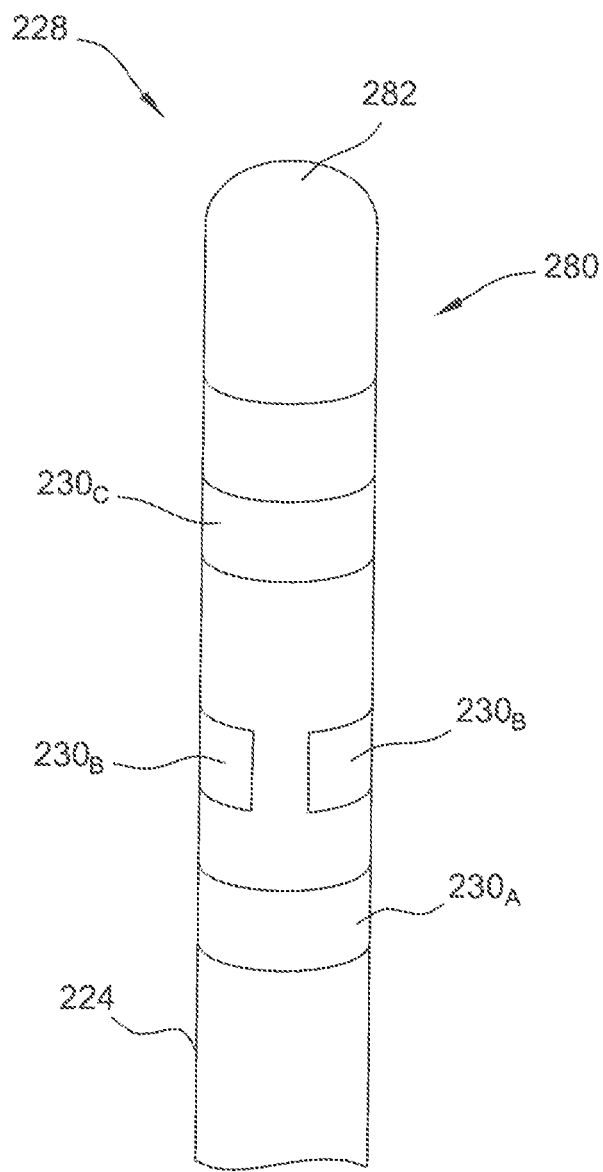
FIG. 4 is a top view of a distal end of one embodiment of a medical device wherein the medical device is a radio frequency (RF) ablation catheter.

Another exemplary embodiment of a high-density electrode catheter is illustrated in FIG. 4. In this embodiment, distal end 228 includes an ablation tip 280, and may be well suited for enhancing radio frequency (RF) ablation procedures. More particularly, the arrangement may allow for the provision of rapid positioning feedback and may also enable updates to be made to HD surface maps as the ablative procedures are being performed.

With continued reference to FIG. 4, in an exemplary embodiment wherein visualization, navigation, and mapping subsystem 218 is an electric field-based system, distal end 228 may include a proximal ring electrode $230_A$ positioned close to, yet spaced apart from, a series of spot or button electrodes $230_B$. Proximal ring electrode $230_A$ and spot electrodes $230_B$ may be used to acquire both EP data and positioning data. Spaced further distally from the spot electrodes $230_B$, a distal ring electrode $230_C$ may be disposed in or on shaft 224 so that bipolar measurements of EP data may be made between the spot electrodes $230_B$ and the distal ring electrode $230_C$. Finally, distal end 228 further includes an ablation electrode 282 for performing ablation therapies, such as, for example and without limitation, RF ablation therapies.

In some embodiments, visualization, navigation, and mapping subsystem 218 includes a magnetic field-based system. For example visualization, navigation, and mapping subsystem 218 may include an electrical field- and magnetic field-based system such as the EnSite™ Precision™ system commercially available from Abbott Laboratories, and generally shown with reference to U.S. Pat. No. 7,263,397 entitled "Method and Apparatus for Catheter Navigation and Location and Mapping in the Heart", the entire disclosure of which is incorporated herein by reference. In such embodiments, distal end 228 may include at least one magnetic field sensor—e.g., magnetic coils (not shown). If two or more magnetic field sensors are disposed near ablation electrode 282, a full six-degree-of-freedom registration of magnetic and spatial coordinates could be accomplished without having to determine orthogonal coordinates by solving for a registration transformation from a variety of positions and orientations. Further benefits of such a configuration may include advanced dislodgement detection and deriving dynamic field scaling since they may be self-contained.

In yet another embodiment of distal end 228 illustrated in FIG. 4, distal ring electrode $230_C$ may be omitted and spot electrodes $230_B$ may be located in its place. As a result, spot electrodes $230_B$ would be closer to ablation electrode 282, which would provide positioning coordinates closer to ablation electrode 282. This in turn may provide for more accurate and precise calculation of the position of ablation electrode 282. Additionally, just as if the distal ring electrode $230_C$ were still in place, a mean signal from the spot electrodes $230_B$ and the proximal ring electrode $230_A$ could still be used to obtain bipolar EP data.

Figure 5:
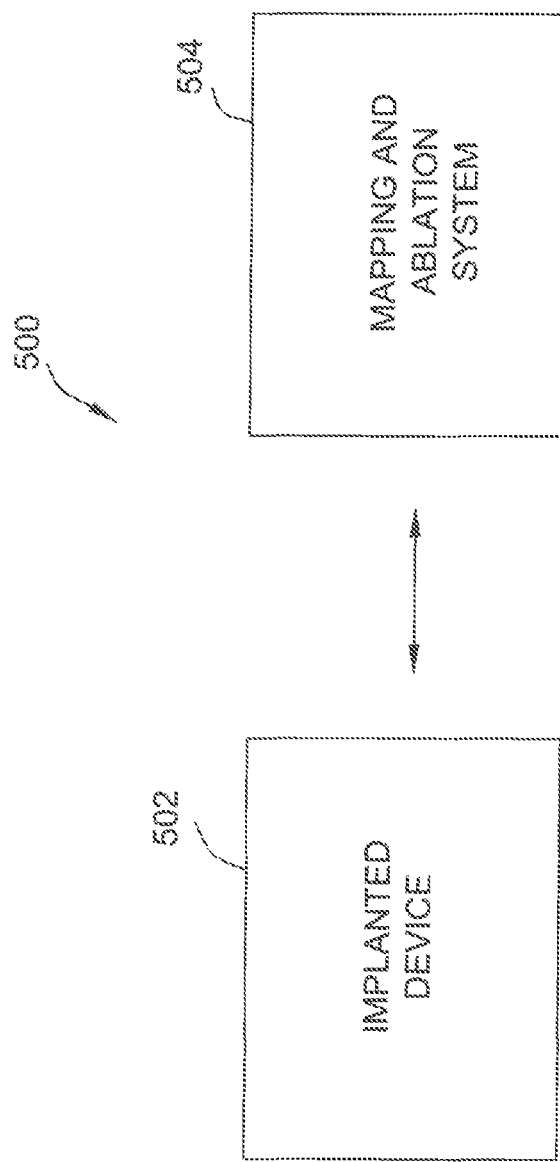
FIG. 5 is a block diagram of one embodiment of a system for determining ablation sites.
Figure 6A:
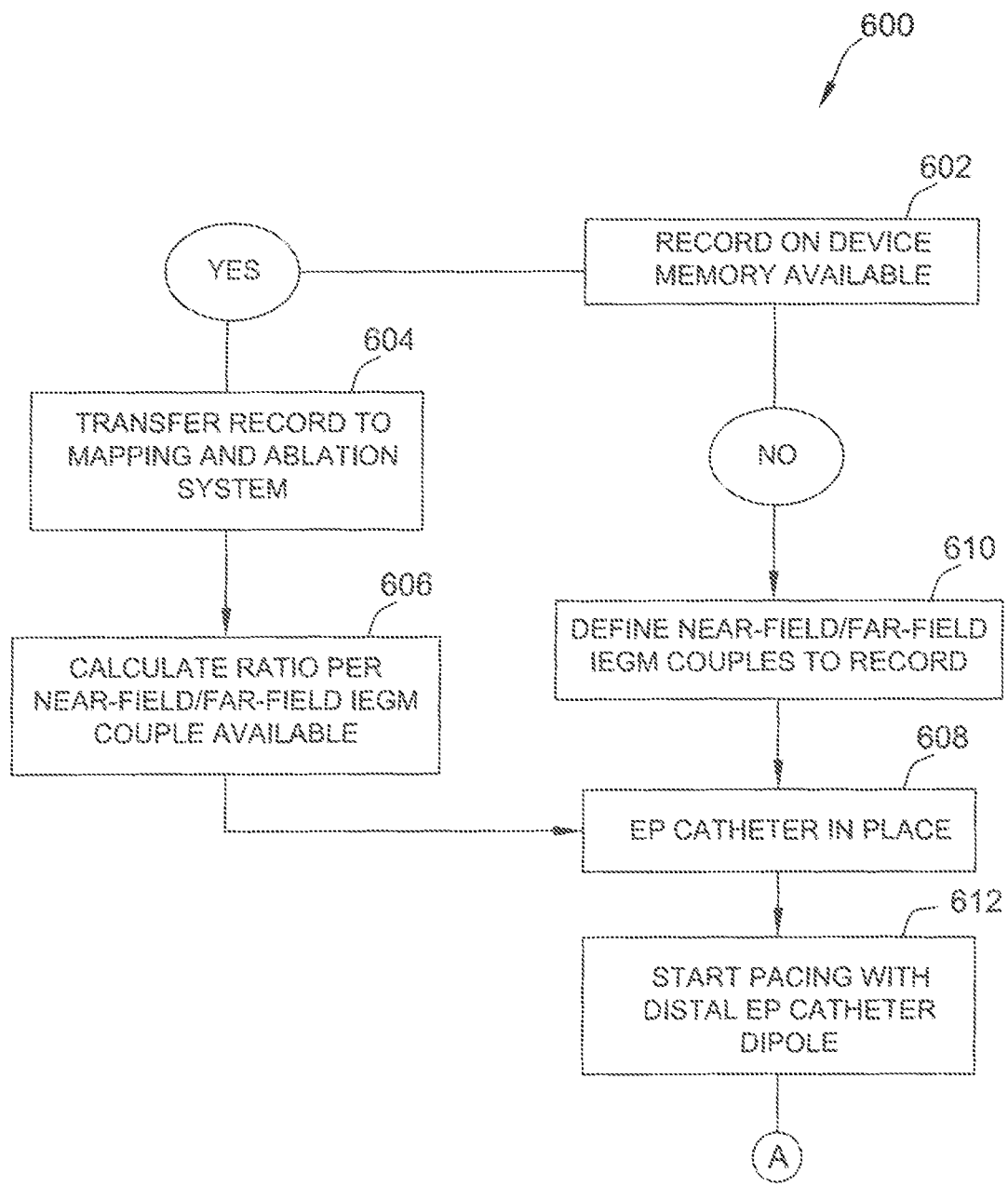
FIGS. 6A-6D are a flow diagram of one embodiment of a method for determining an ablation site that may be used with the system shown in FIG. 5.
Figure 6B:
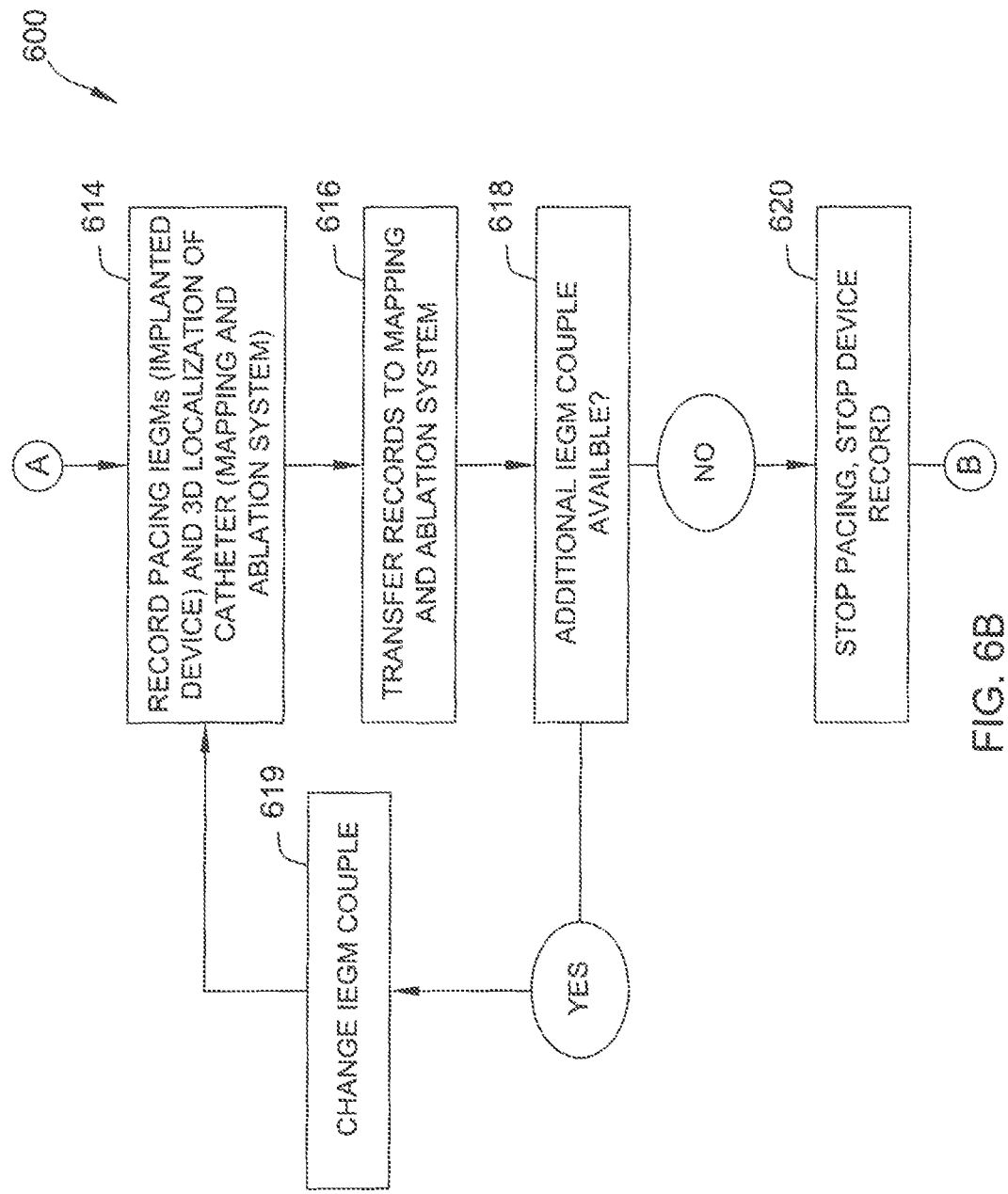
Figure 6C:
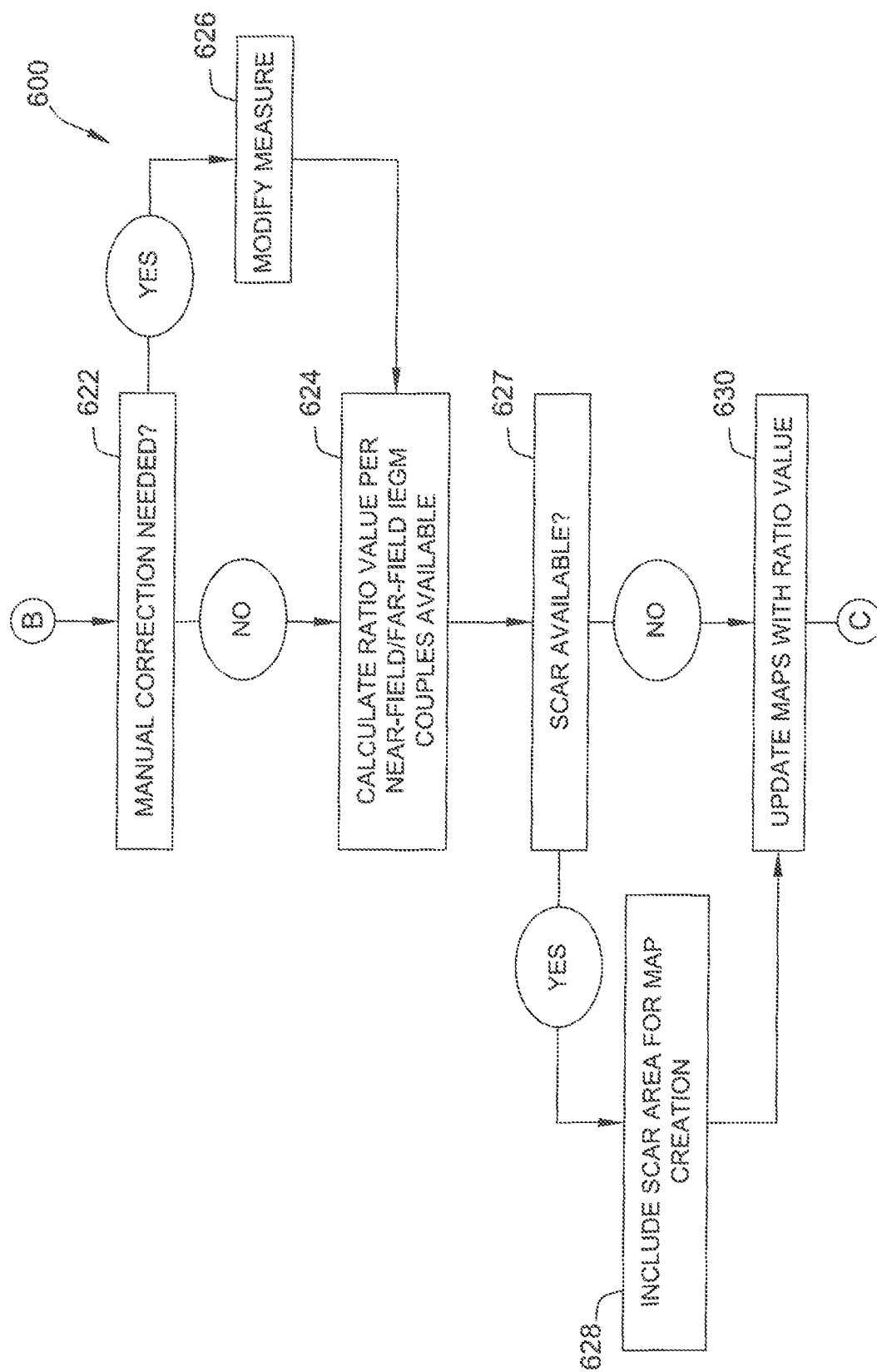
Figure 6D:
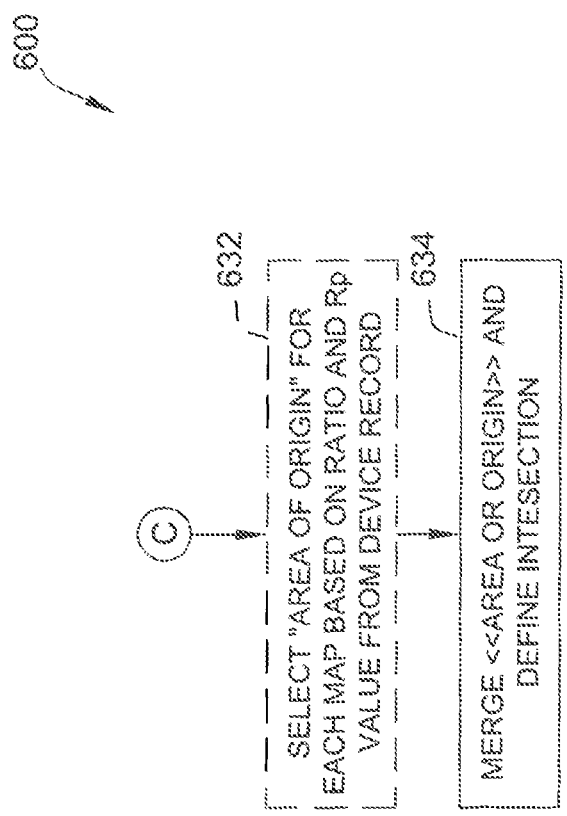

FIG. 5 is block diagram of a system 500 for determining one or more proposed ablation sites. System 500 includes an implanted device 502, such as pacemaker/ICD 100 (shown in FIGS. 1A and 1B) communicatively coupled to a mapping and ablation system 504, such as mapping and ablation system 210 (shown in FIG. 2). Implanted device 502 and mapping and ablation system 504 may be communicatively coupled to one another using any suitable wired and/or wireless communication scheme. For example, implanted device 502 and mapping and ablation system 504 may communicate using radio frequency (RF) communications, such as those used by the Merlin@Home® system (Merlin@home is a registered trademark of Pacesetter, Inc. of Sylmar, Calif.). As described herein, IEGMs registered by implanted device 502 are leveraged to determine locations to ablate with system 504.

More specifically, using the systems and methods described herein, a number of time related measurements are defined for various IEGM couples (described below) during an EP examination, and those measurements are compared to propose one or more specific ventricular sites for ablating to treat a patient rhythm disorder. This enables a physician to target responsible sites more quickly and with increased confidence. Information may also be transmitted from mapping and ablation system 504 to implanted device 502 to improve patient management and future diagnostics.

The systems and methods described herein facilitate interfacing and transmitting signals between implanted device 502 and mapping and ablation system 504. Further, the systems and methods described herein facilitate recording and storing specific IEGM signals and/or measurements. The embodiments described also herein facilitate analyzing endocardiac signals obtained by implanted device 502 during spontaneous arrhythmia of a patient and in the framework of voluntary cardiac catheter stimulations at specified cardiac sites during an EP examination. In addition, sites that are likely to be the origin of clinical arrhythmia in a patient can be indicated in a 3D mapping generated by mapping and ablation system 504.

In the exemplary embodiment, implanted device 502 measures and records at least one IEGM couple. As used herein, an "IEGM couple" refers to a near-field IEGM and a far-field IEGM. The two IEGMs in the couple are recorded in a synchronized manner in the exemplary embodiment. The following Table 1 provides a number of exemplary IEGM couples. Those of skill in the art will appreciate that the IEGM couples listed in Table 1 are merely exemplary, and do not constitute an exhaustive list.

TABLE 1

| Near Field IEGM | | Far Field IEGM | |
|---|---|---|---|
| Cathode | Anode | Cathode | Anode |
| RVd | RVp | RVd | CAN |
| RVd | RVp | RVd | RVcoil |
| RVd | RVp | RVcoil | CAN |
| LVd | LVm2 | LVd | RVd |

TABLE 1-continued

| Near Field IEGM | | Far Field IEGM | |
|---|---|---|---|
| Cathode | Anode | Cathode | Anode |
| LVd | LVm2 | LVd | RVcoil |
| LVd | LVm2 | LVd | LVp |
| LVm3 | LVp | LVd | RVd |
| LVm3 | LVp | LVd | RVcoil |
| LVm3 | LVp | LVd | LVp |

In Table 1, RV refers to right ventricular lead 130 (shown in FIG. 1A), and LV refers to left ventricular lead 124 (also shown in FIG. 1A). Further, d refers to the distal pole of the associated lead (i.e., ventricular tip electrode 132 or LV electrode $126_1$), p refers to the proximal pole of the associated lead (i.e., RV ring electrode 134 or LV electrode $126_4$), coil refers to RV coil electrode 136, and m2 and m3 refer to LV electrodes $126_2$ and $126_3$, respectively. The various leads and electrodes are further described above with reference to FIGS. 1A and 1B.

In the example embodiment, two values are measured for each IEGM couple: i) a time from a far field initial signal to a near field main deflection (represented as Dact(iegm1, iegm2)); and ii) a time from the far field initial signal to an end of the signal (represented as W(iegm1, iegm2)). From these two values, in the exemplary embodiment, a ratio R is calculated (for each IEGM couple) as R(iegm1, iegm2)= Dact(iegm1, iegm2)/W(iegm1, iegm2).

FIGS. 6A-6D are a flow diagram of a method 600 for determining an ablation site. Method 600 may be implemented, for example, using implanted device 502 and mapping and ablation system 504 (both shown in FIG. 5).

At block 602, it is determined whether any IEGM couples are already stored on a memory of the implanted device. If there are IEGM couples previously stored on the implanted device, flow proceeds to block 604, and the previously stored IEGM couples are transmitted to the mapping and ablation system. In the exemplary embodiment, signals recorded by the implanted device, as well as the associated IEGM vector definitions (e.g., Rvd-Rvp; Rvd-Can . . . etc.) are transmitted. Further, synchronized IEGM couples are transmitted to conserve synchronization.

After the IEGM couples are transmitted, the ratio for each IEGM couple is calculated at block 606. The ratio may be calculated, for example, by a processing device included in the mapping and ablation system. Flow then proceeds to block 608, where an EP catheter of the mapping and ablation system is positioned within the patient (e.g., by the physician).

From block 602, if there are no IEGM couples previously stored on the implanted device, flow proceeds to block 610, in which the IEGM couples to be recorded are defined. In the exemplary embodiment, the IEGM couples are defined at the implanted device (as opposed to the mapping and ablation system). Alternatively, the IEGM couples may be defined in any manner that enables method 600 to be implemented as described herein. Flow then proceeds to block 608.

From block 608, flow proceeds to block 612, and the EP catheter initiates pacing (e.g., using a distal dipole of the EP catheter). Pacing may be performed, for example, at three or more locations within a cardiac chamber of interest. At block 614, the IEGM couples are recorded by the implanted device during the pacing, and the three-dimensional location of the EP catheter is recorded by the mapping and ablation system. In the exemplary embodiment, a relatively low number (e.g., less than 5) of cardiac cycles are observed for each IEGM couple. At block 616, the recorded IEGM couples are transmitted from the implanted device to the mapping and ablation system. The IEGM couples may be transmitted automatically, or in response to a user input (e.g., received at the mapping and ablation system). At block 618, it is determined whether there are any remaining IEGM couples to be recorded. If so, the IEGM couple being recorded is updated at block 619, and flow returns to block 614. If not, flow proceeds to block 620, and pacing and recording are ended.

At block 622, it is determined whether manual correction is needed to the recorded IEGM couples. For example, manual correction may be used to adjust the position of automatic detections in situations where irregular morphology (or other factors) cause automatic detections that result in incorrect IEGM couples and/or calculated ratios. If manual correction is not needed, flow proceeds to block 624, and the ratio value is calculated for each IEGM couple. If manual correction is needed, flow proceeds to block 626, the IEGM detections or events are modified appropriately, and flow then proceeds to block 624. For example, if data is recorded for multiple electrical cardiac events, the results from the multiple events may be averaged.

At block 627, it is determined (e.g., by the mapping and ablation system), whether scar data (i.e., data specifying an anatomical location of one or more scars) is available. If scar data is available, that scar data is included (at block 628) in maps generated by the mapping and ablation system. If no scar data is available, flow proceeds directly to block 630, and maps generated by the mapping and ablation system are updated to include the calculated ratio values. As will be appreciated by those of skill in the art, interpolation is used to generate values for locations between "measured" points. In the exemplary embodiment, a map is created for each IEGM couple. Alternatively, any suitable number and type of maps may be generated.

Flow proceeds from block 630 to block 632. At block 632, an area of origin is determined for each map (i.e., for each IEGM couple) based on the calculated ratio, also referred to as Rp, values recorded by the implanted device. For example, a first set of ratios may calculated for each IEGM couple during spontaneous VT, and a second set of ratios may be calculated for each IEGM while a physician applies pacing at a predetermined location. Because the location of the spontaneous VT is unknown, the ratios obtained at pacing sites are compared with the ratios obtained during spontaneous VT.

The size of each area of origin generally depends on the number of pacing sites and/or a precision value (Pr) defined by the user (e.g., the physician). The Pr can be input by the user (e.g., input into the mapping and ablation system) and is a positive or negative value from the calculated ratio. Specifically, in the exemplary embodiment, all areas on the map having a similar ratio plus or minus the Pr are included in the area of origin.

At block 634, the areas of origin are superimposed to define an intersection. The resulting intersection is an area from which the VT likely originates, and accordingly, corresponds to a proposed ablation location. For example, suppose the ratios obtained during spontaneous VT define a first area, and the ratios obtained during pacing define a second area. The region defined by the intersection of the first and second areas then represents an area from which VT likely originates. Said another way, if a ratio for a particular IEGM couple that is calculated during pacing is relatively close to a corresponding ratio for that particular IEGM couple that is calculated during spontaneous VT, the location of the pacing is close to the origin of spontaneous VT. Accordingly, to treat the VT, the physician may ablate the proposed ablation location. In some embodiments, the map may also include representations of past VT occurrences (e.g., over the last six months or year), providing further guidance to the physician as to the most active regions.

In some embodiments, based on the proposed ablation location, the mapping and ablation system may propose new IEGM couples for future use. This may be accomplished, for example, by defining a dedicated set of IEGM couples for different spatial locations (e.g., basal, mid apical, septal, non-septal, etc.). For example, if the VT origin is determined to be the basal region, the physician may reprogram implanted device 502 to store a pertinent IEGM couple. If a new VT subsequently occurs, implanted device 502 will record that IEGM couple. This may be implemented, for example, using a look-up table that lists a plurality of potential VT locations, and a pertinent IEGM couple associated with each potential VT locations. Further, if no previous VT origin is determined, or if the physician wants to 'reset' system 500, a baseline IEGM record may be stored, the baseline IEGM generally useful for determining VT origins at a variety of spatial locations.

Further, in some embodiments, if the patient experiences arrhythmia during the EP exam, the IEGM couples and calculated ratios can be transmitted from the mapping and ablation system to the implanted device. The IEGM couples and calculated ratios may be stored on the implanted device for additional usage (e.g., for extraction during future EP exams, for comparison with future arrhythmias, etc.).

FIGS. 7-11 illustrate one example of determining a proposed ablation site using IEGM couples. In this example, a calculated parameter is defined as R(x,y), where the first index, x, is representative of the IEGM couple used to calculate the R value, and where the second index, y, is representative of the pacing site used to obtain the IEGM couple (when the ratio is calculated during pacing). For spontaneously recorded VT, the second index is indicated as 'spont'. In this example, three different pacing sites and two different IEGM couples are used. Those of skill in the art will appreciate that any suitable number of pacing sites and IEGM couples may be used.

Figure 7:
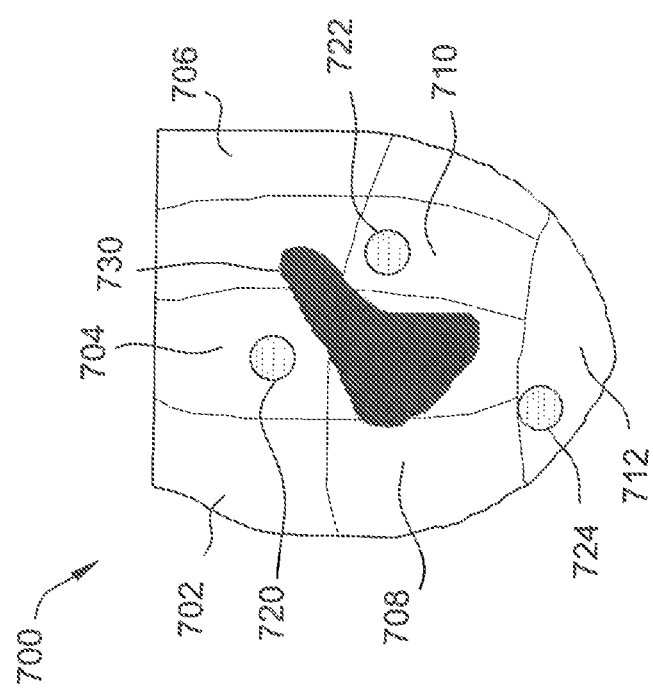
FIG. 7 is a schematic diagram of the left ventricle.

FIG. 7 is a schematic diagram of the left ventricle 700. Left ventricle 700 includes a plurality of different anatomical regions, such as a septal basal region 702, a posterior basal region 704, an anterior basal region 706, a septal mid region 708, a lateral mid region 710, and an apex region 712. A first pacing site 720 (i.e. pacing site (a)), a second pacing site 722 (i.e., pacing site (b)), and a third pacing site 724 (i.e., pacing site (c)) are indicated in FIG. 7. Further, a scar zone 730 is also indicated.

In this example the first IEGM couple is (Rvd-Rvp; Rvd-Rvcoil), and the second IEGM couple is (Rvd-Rvp; Rvd-Can). Accordingly, for two IEGM couples and three pacing sites, six different R(x,y) parameters can be calculated, as listed in the following Table 2:

TABLE 2

|  | Site (a) | Site (b) | Site (c) |
| --- | --- | --- | --- |
| IEGM Couple 1 | R(1, a) | R(1, b) | R(1, c) |
| IEGM Couple 2 | R(2, a) | R(2, b) | R(2, c) |

Figure 8:
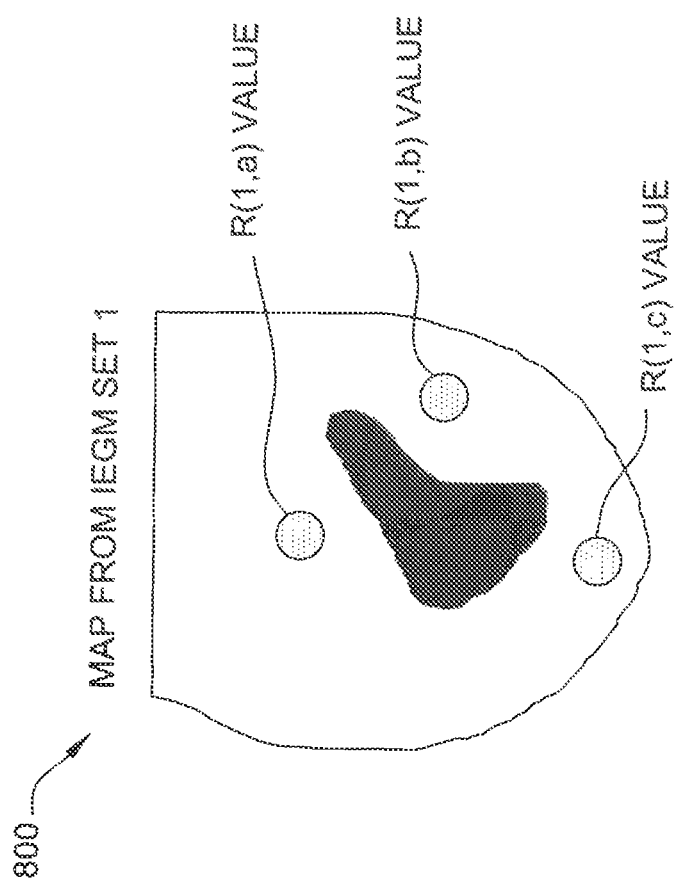
FIGS. 8 and 9 are schematic diagrams illustrating the locations associated with calculated parameters for determining ablation sites.
Figure 9:
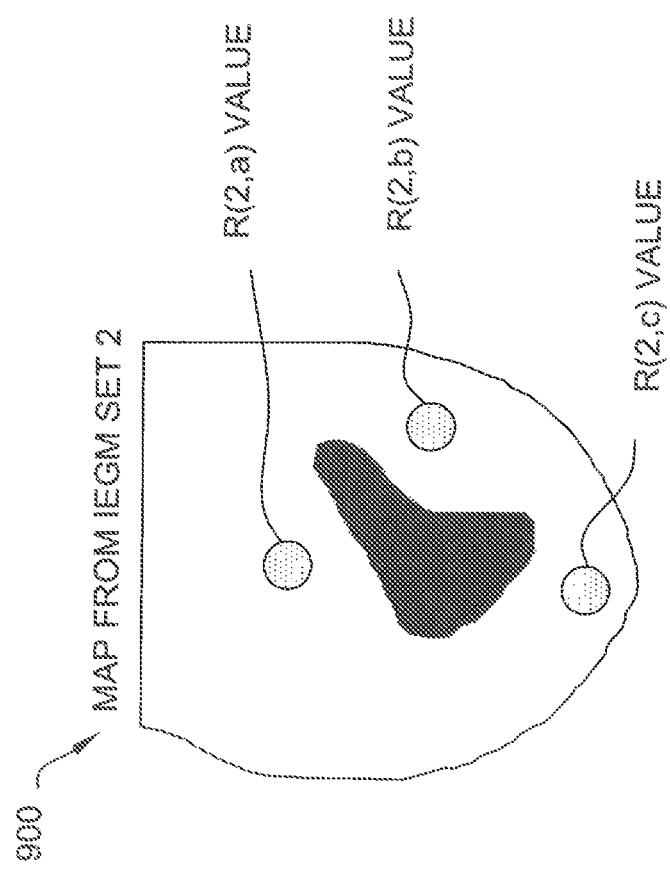
Figure 10:
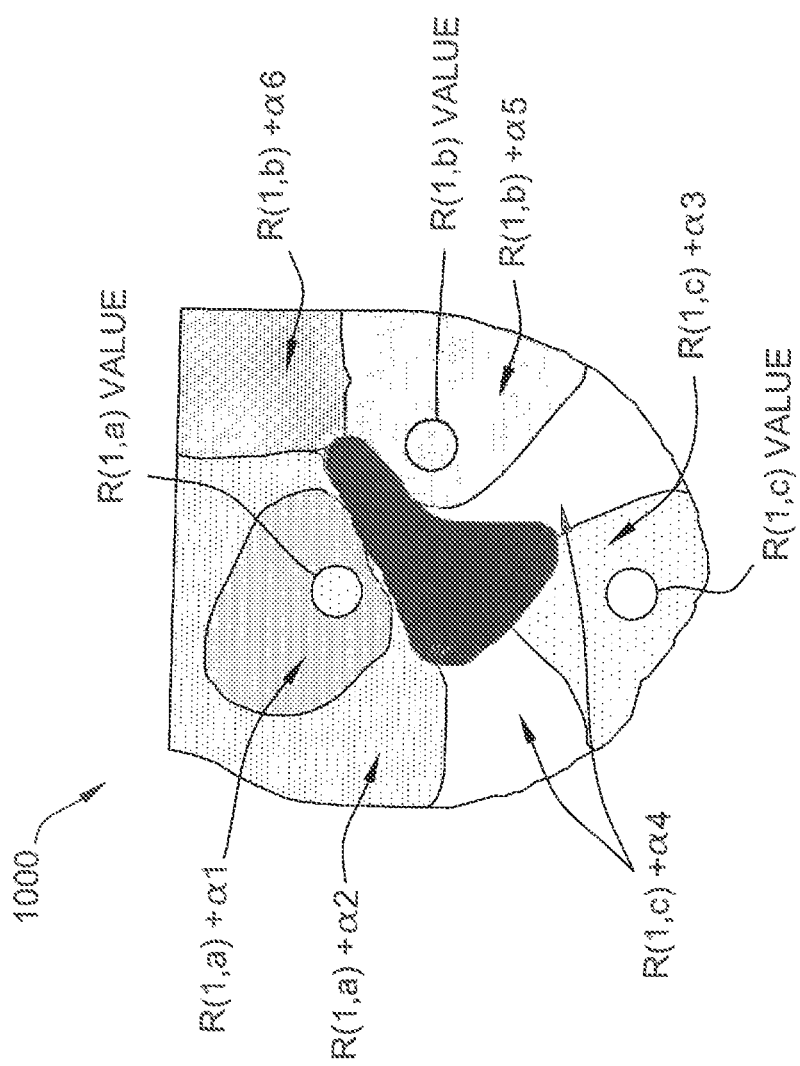
FIG. 10 is a schematic diagram illustrating interpolated regions.

FIGS. 8 and 9 are schematic diagrams 800 and 900 illustrating the locations associated with the six R(x,y)

parameters. Further, as will be appreciated by those of skill in the art, interpolation methods may be used to assign values to locations that are not pacing sites. For example, FIG. 10 is a schematic diagram 1000 illustrating interpolated regions.

Figure 11:
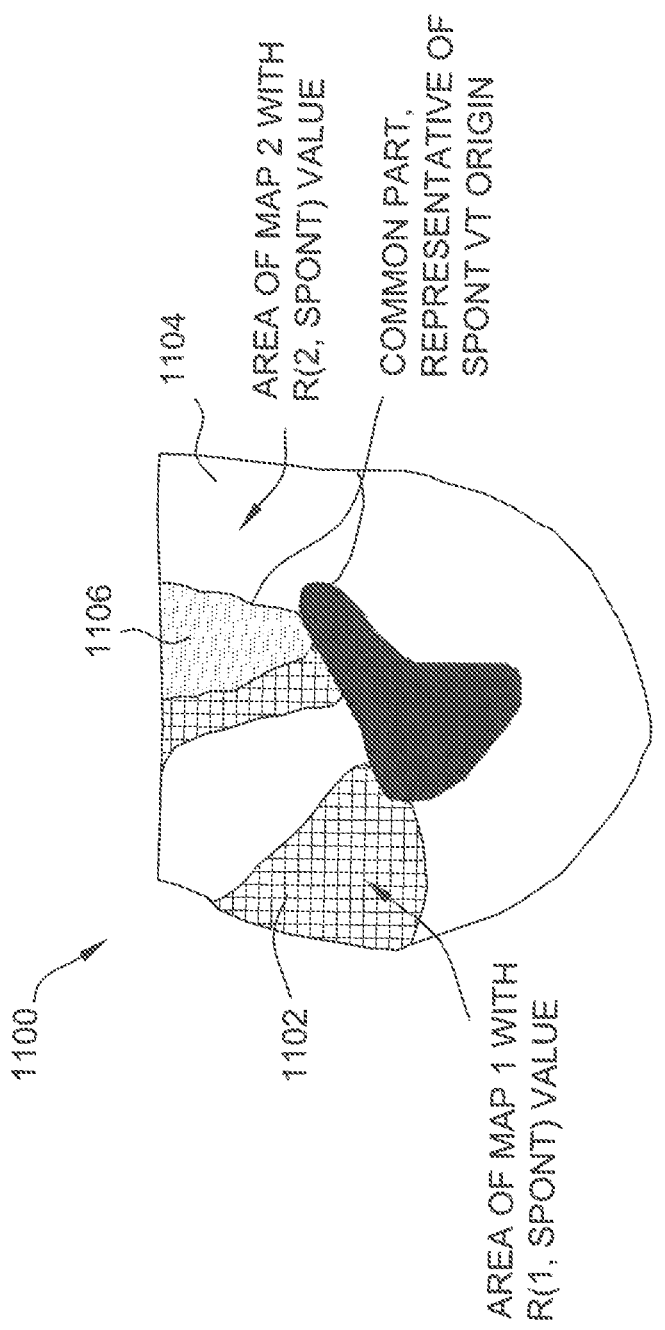
FIG. 11 is a schematic diagram illustrating the use of calculated parameters to determine a proposed ablation site.

FIG. 11 illustrates using the calculated R(x,y) parameters to determine a proposed ablation site. As shown in FIG. 11, a first area of origin 1102 corresponds to regions that have a calculated parameter of R(1,spont). Similarly, a second area of origin 1104 corresponds to regions that have a calculated parameter of R(2,spont). The overlap between first and second area of origins 1102 and 1104 defines an intersection region 1106, and intersection region 1106 identifies a proposed ablation location.

Accordingly, the systems and method described herein facilitate determining a proposed ablation site in a cardiac chamber. An implanted device records a plurality of intracardiac electrogram (IEGM) couples. A mapping and ablation system communicatively coupled to the implanted device receives the recorded plurality of IEGM couples from the implanted device, and calculates a parameter for each of the plurality of IEGM couples. Based on the calculated parameters, the mapping and ablation system determines an area of origin for each IEGM couple, and determines an intersection between the determined areas of origin, the intersection representing the proposed ablation site in the cardiac chamber.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for determining a proposed ablation site in a cardiac chamber, the system comprising:
   an implanted device configured to record a plurality of intracardiac electrogram (IEGM) couples; and
   a mapping and ablation system communicatively coupled to the implanted device, the mapping and ablation system including a controller configured to:
   receive the recorded plurality of IEGM couples from the implanted device;
   calculate a parameter for each of the plurality of IEGM couples;
   determine, based on the calculated parameters, an area of origin for each IEGM couple; and
   determine an intersection between the determined areas of origin, wherein the intersection represents the proposed ablation site in the cardiac chamber.

2. The system of claim 1, wherein each IEGM couple includes a near-field IEGM and a far-field IEGM.

3. The system of claim 1, wherein the implanted device is an implantable cardioverter defibrillator.

4. The system of claim 1, wherein the mapping and ablation system is communicatively coupled to the implanted device using a wireless communication scheme.

5. The system of claim 1, wherein the mapping and ablation system is further configured to:
   generate a map of the cardiac chamber including the proposed ablation site; and
   display the generated map.

6. The system of claim 5, wherein the generated map includes scar data.

7. The system of claim 1, wherein the implanted device is further configured to define, based on user input, the plurality of IEGM couples to be recorded.

8. The system of claim 1, wherein the parameter includes at least one of i) a time from a far field initial signal to a near field main deflection or ii) a time from the far field initial signal to an end of the signal.

9. The system of claim 1, wherein the area of origin for at least one of the IEGM couples is determined based on a ratio between time measures for signals from the corresponding IEGM couples.

10. A mapping and ablation system for determining a proposed ablation site in a cardiac chamber, the mapping and ablation system comprising:
    a memory device; and
    a processor communicatively coupled to the memory device, the processor configured to:
    receive a plurality of intracardiac electrogram (IEGM) couples recorded by an implanted device;
    calculate a parameter for each of the plurality of IEGM couples;
    determine, based on the calculated parameters, an area of origin for each IEGM couple; and
    determine an intersection between the determined areas of origin, wherein the intersection represents the proposed ablation site in the cardiac chamber.

11. The mapping and ablation system of claim 10, wherein each IEGM couple includes a near-field IEGM and a far-field IEGM.

12. The mapping and ablation system of claim 10, wherein the implanted device is an implantable cardioverter defibrillator.

13. The mapping and ablation system of claim 10, wherein the mapping and ablation system is communicatively coupled to the implanted device using a wireless communication scheme.

14. The mapping and ablation system of claim 10, wherein the mapping and ablation system is further configured to:
    generate a map of the cardiac chamber including the proposed ablation site; and
    display the generated map.

15. The mapping and ablation system of claim 14, wherein the generated map includes scar data.

16. The mapping and ablation system of claim 10, wherein the parameter includes at least one of i) a time from a far field initial signal to a near field main deflection or ii) a time from the far field initial signal to an end of the signal.

17. The mapping and ablation system of claim 10, wherein the area of origin for at least one of the IEGM couples is determined based on a ratio between time measures for signals from the corresponding IEGM couples.

18. A method for determining a proposed ablation site in a cardiac chamber, the method comprising:
   receiving, at a mapping and ablation system, a plurality of intracardiac electrogram (IEGM) couples recorded by an implanted device;
   calculating, using the mapping and ablation system, a parameter for each of the plurality of IEGM couples;
   determining, using the mapping and ablation system, based on the calculated parameters, an area of origin for each IEGM couple; and
   determining, using the mapping and ablation system, an intersection between the determined areas of origin, wherein the intersection represents the proposed ablation site in the cardiac chamber.

19. The method of claim 18, wherein each IEGM couple includes a near-field IEGM and a far-field IEGM.

20. The method of claim 18, wherein the mapping and ablation system receives the plurality of intracardiac electrogram (IEGM) couples from the implanted device using a wireless communication scheme.

21. The method of claim 18, further comprising:
   generating a map of the cardiac chamber including the proposed ablation site; and
   displaying the generated map.

22. The method of claim 21, wherein generating a map comprises generating a map including scar data.

23. The method of claim 18, wherein the parameter includes at least one of i) a time from a far field initial signal to a near field main deflection or ii) a time from the far field initial signal to an end of the signal.

24. The method of claim 18, wherein the area of origin for at least one of the IEGM couples is determined based on a ratio between time measures for signals from the corresponding IEGM couples.

* * * * *